United States Patent
Karim et al.

(10) Patent No.: US 10,856,826 B2
(45) Date of Patent: Dec. 8, 2020

(54) METHOD AND SYSTEM FOR DETERMINING VIRTUAL OUTPUTS FOR A MULTI-ENERGY X-RAY IMAGING APPARATUS

(71) Applicant: KA Imaging Inc., Kitchener (CA)

(72) Inventors: Karim S. Karim, Kitchener (CA); Sebastian Lopez Maurino, Kitchener (CA); Sina Ghanbarzadeh, Kitchener (CA)

(73) Assignee: KA IMAGING INC., Ontario (CA)

( * ) Notice: Subject to any disclaimer, the term of this patent is extended or adjusted under 35 U.S.C. 154(b) by 0 days.

(21) Appl. No.: 16/436,098

(22) Filed: Jun. 10, 2019

(65) Prior Publication Data

US 2019/0374182 A1  Dec. 12, 2019

Related U.S. Application Data

(60) Provisional application No. 62/682,540, filed on Jun. 8, 2018.

(51) Int. Cl.
*A61B 6/00* (2006.01)

(52) U.S. Cl.
CPC ............ *A61B 6/482* (2013.01); *A61B 6/4208* (2013.01); *A61B 6/4266* (2013.01); *A61B 6/505* (2013.01); *A61B 6/5205* (2013.01); *A61B 6/5282* (2013.01)

(58) Field of Classification Search
CPC ..... A61B 6/4208; A61B 6/4266; A61B 6/482; A61B 6/505; A61B 6/5205; A61B 6/5282
See application file for complete search history.

(56) References Cited

U.S. PATENT DOCUMENTS

2016/0302751 A1*  10/2016  Grant ................... A61B 6/5205

* cited by examiner

*Primary Examiner* — Mark R Gaworecki
(74) *Attorney, Agent, or Firm* — Gowling WLG (Canada) LLP; Jeffrey W. Wong

(57) ABSTRACT

The disclosure is directed at a method and apparatus for determining virtual outputs for a multi-energy x-ray apparatus. Based on the application that the x-ray apparatus is being used for, a general algorithm can be determined or selected. Inputs received from the x-ray apparatus can be substituted into the general algorithm to generate a virtual output algorithm for the x-ray apparatus. Virtual outputs can then be calculated using the virtual output algorithm.

23 Claims, 12 Drawing Sheets

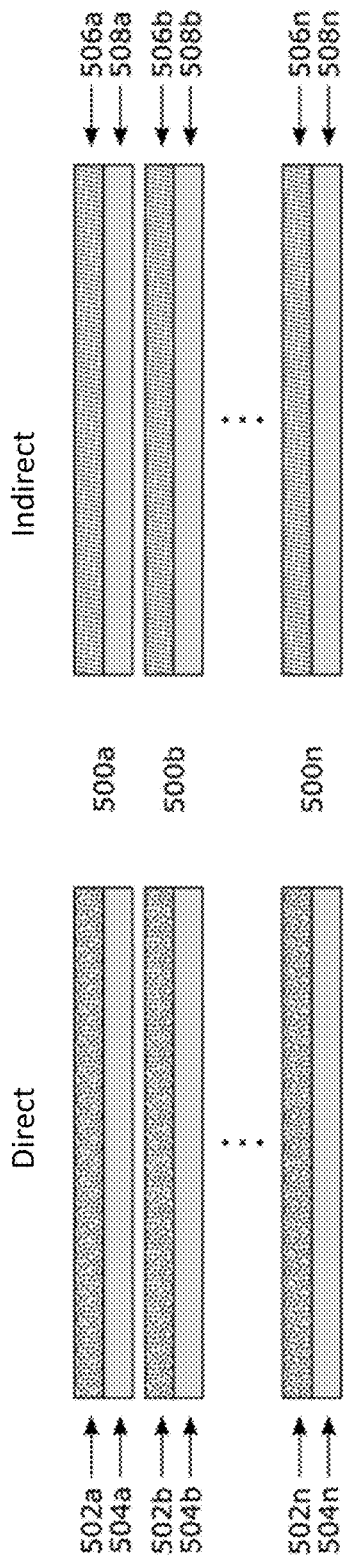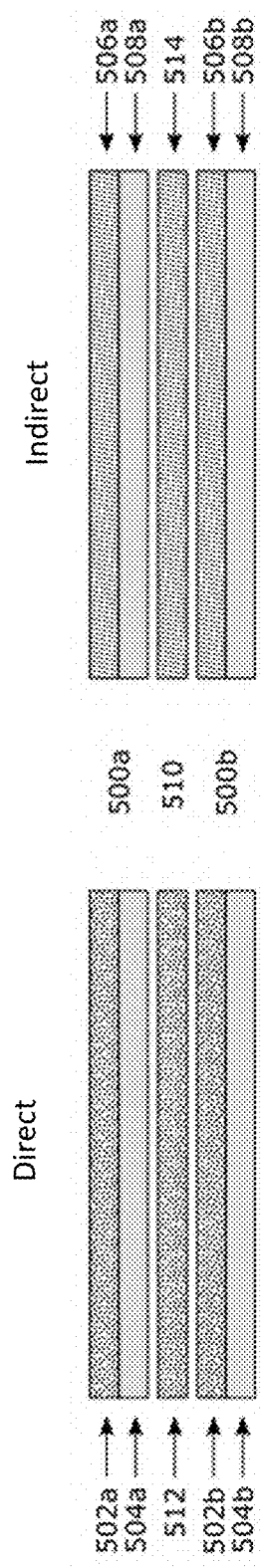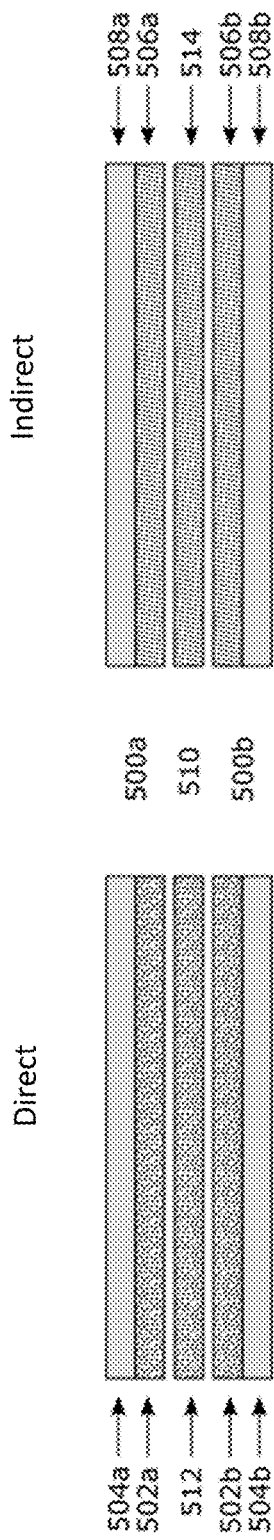
Figure 5
Figure 6a
Figure 6b

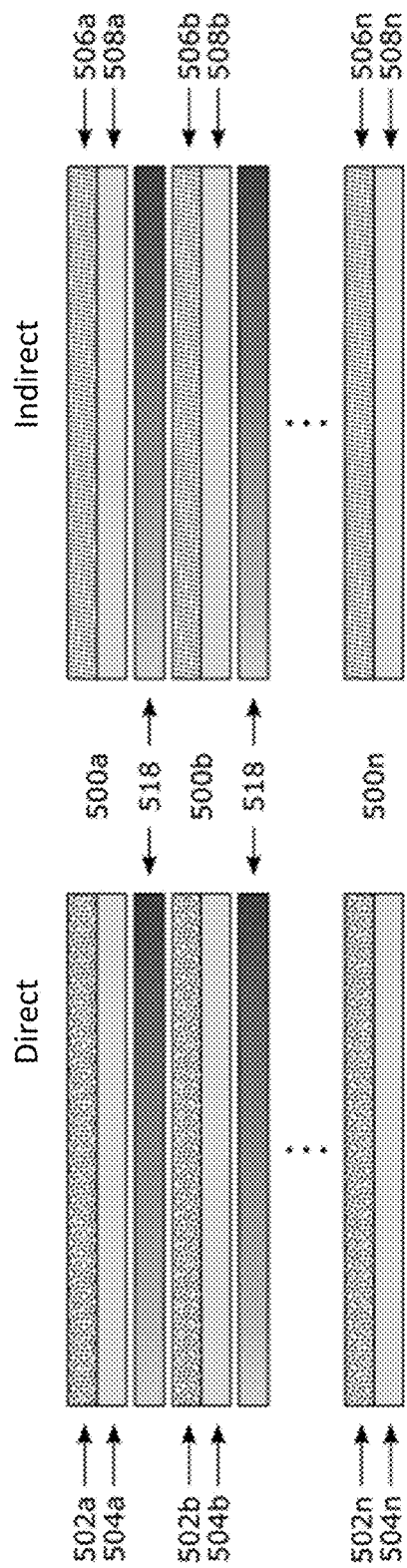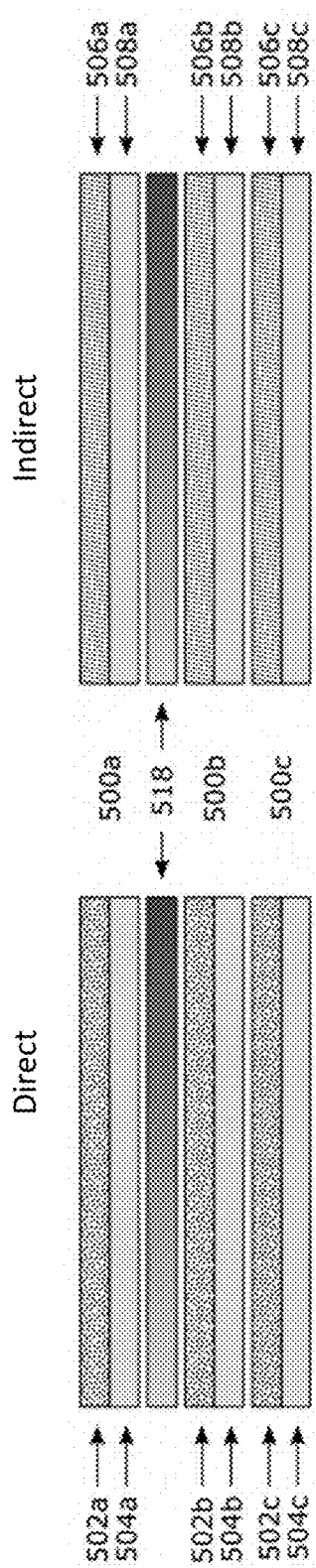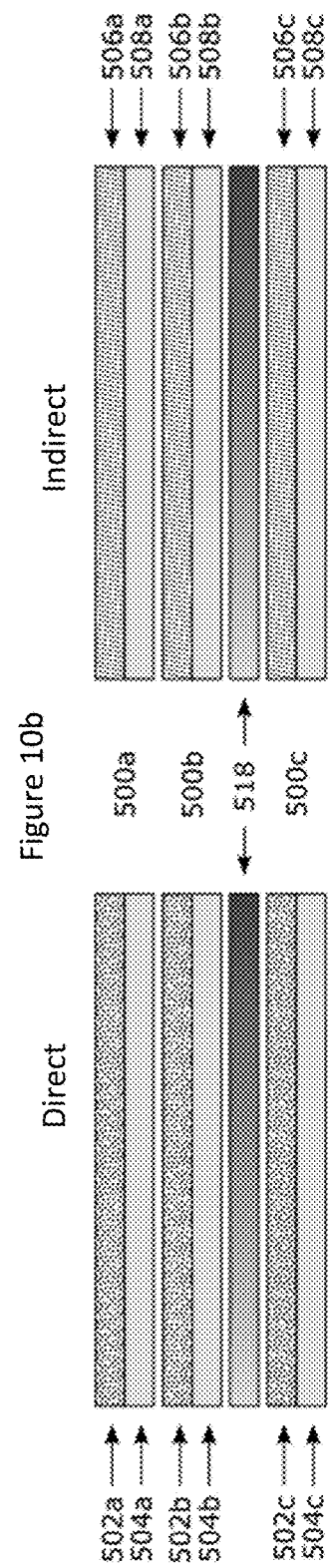

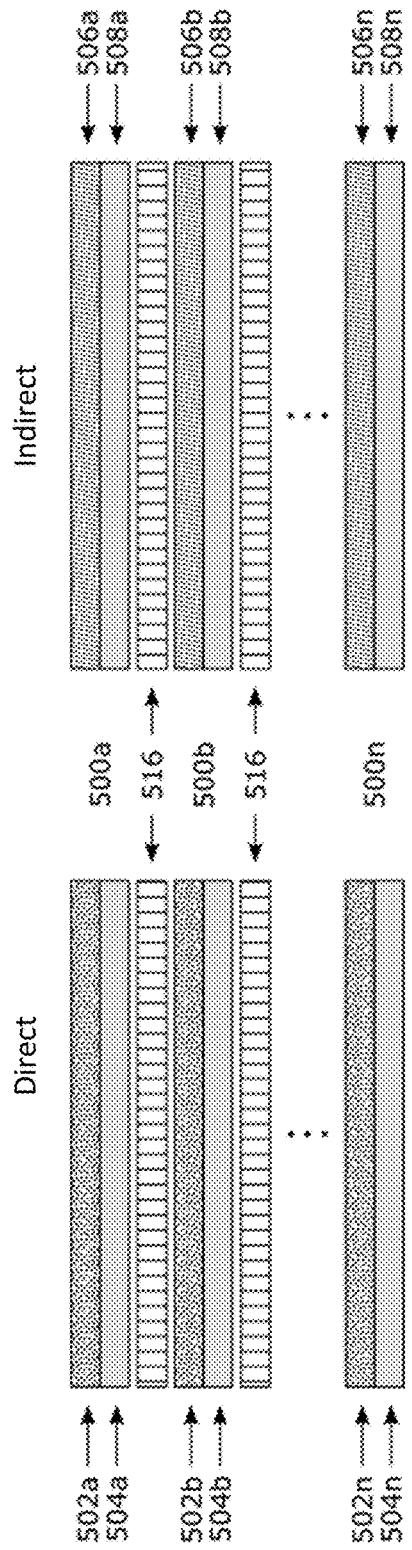
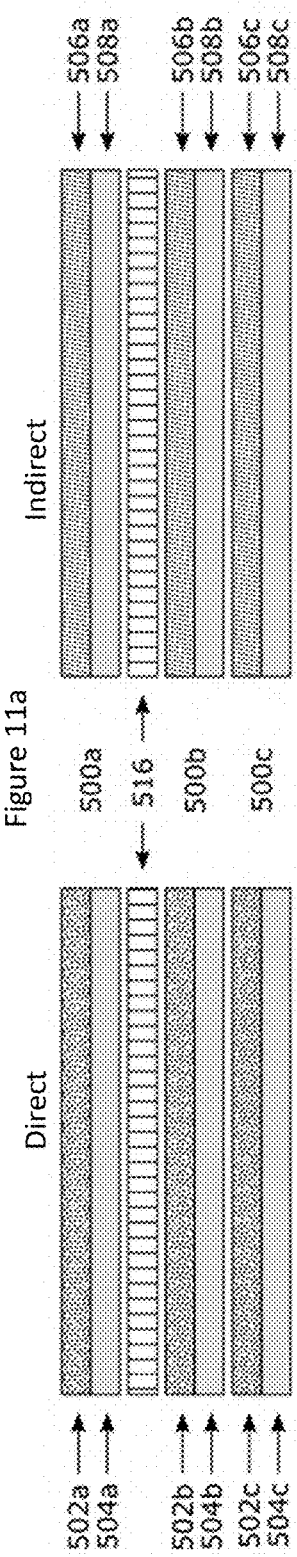
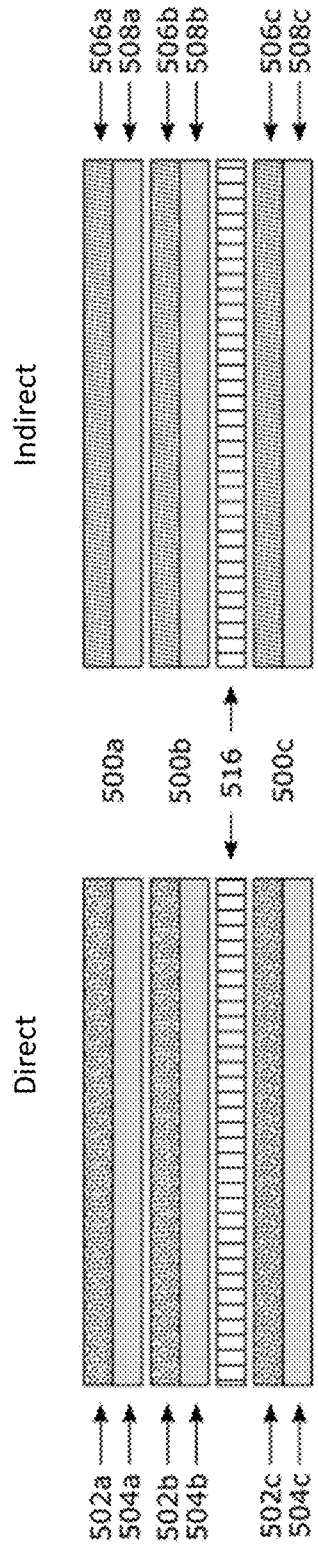
Figure 11a
Figure 11b
Figure 11c

METHOD AND SYSTEM FOR DETERMINING VIRTUAL OUTPUTS FOR A MULTI-ENERGY X-RAY IMAGING APPARATUS

CROSS-REFERENCE TO OTHER APPLICATIONS

This application claims priority from U.S. Provisional Application No. 62/682,540 filed Jun. 8, 2018 the contents of which are hereby incorporated by reference.

FIELD OF THE DISCLOSURE

The disclosure is generally directed at x-ray imaging and, more specifically, at a method and system for determining virtual outputs for a multi-energy x-ray imaging apparatus.

BACKGROUND OF THE DISCLOSURE

The quality of a medical image and by extension its value as a tool depends only on how well it can convey the anatomy of the patient being imaged to the observer, such as a physician. The better the anatomy is understood, the more accurate information the physician has to make decisions.

In x-ray imaging, a large source of noise that often decreases the quality of an image is anatomical noise. It is caused by a superposition of the normal anatomy that stems from the two-dimensional (2D) projection of the three-dimensional (3D) patient. This noise can obscure the tissue being imaged or can be misread as anatomical abnormalities. A simple example of this is a chest radiograph that is acquired with the intention of evaluating pulmonary anatomy, which is inevitably obstructed by the ribs in the obtained image. In this case, the ribs are a major source of anatomical noise, as they are not the anatomy of interest.

A technique that was proposed to reduce anatomical noise is Dual-Energy (DE) Imaging. This technique exploits a fundamental property of x-ray and matter interaction: not only will different tissue types have different mass attenuation coefficients ($\mu/\rho(E)$) across the diagnostic energy range, but the rate of change of these coefficients will also differ.

One challenge in DE imaging comes from the need to obtain two separate low and high energy images. To achieve this, the x-ray spectrum that is absorbed at the detector should be heavily weighted in the low-end of the diagnostic range for the low-energy (LE) image, and in the high-end for the high energy (HE) image. DE imaging is able to decompose the patient's projection into soft-tissue- and hard-tissue-only images. Several mathematical methods exist for obtaining these DE images from the LE and HE inputs, most notably logarithmic subtraction and basis decomposition.

In practice, a total cancellation of a specific tissue type is not commonly possible. Several factors contribute to form a non-ideal scenario that cannot be captured by mathematical techniques. These include: the broad spectrum of x-ray fluences that will lead to the formation of each image as opposed to the idealized sources used in the mathematical analysis; inhomogeneities in the density or mass attenuation coefficient of the tissue being canceled which make it impossible to determine the exact value that should be used when calculating the weighting factor; and x-ray scatter from both the object being imaged and the detector that are not accounted by Beer-Lambert law. These non-idealities also mean that the theoretical value of the weighting factors may not provide the best possible cancellation, requiring the observer to calculate their ideal value experimentally or qualitatively.

Obtaining this spectral separation in practice is achieved in two fundamentally different ways: either the source spectrum differs for the two images (referred to hereon as multi-shot DE imaging), or the detector selectively absorbs different parts of a wider spectrum to form each image (referred to hereon as single-shot DE imaging). Regardless of the method used, a large separation of the two spectra is imperative in obtaining high quality tissue-selective images.

One approach to obtain images at different energies is to acquire temporally sequentially, changing no part of the imaging system but the spectrum the x-ray tube generates. This is the concept behind multi-shot imaging (sometimes called kVp switching), where a first image is taken using a low x-ray tube kVp and, immediately after, a second image is obtained with a high kVp. Since the low and high kVp beams will have different effective energies, the two resulting images will contain mainly information obtained in the low and high ends of the x-ray diagnostic spectrum, respectively. Alternatively, instead of modifying source kVp between exposures it is possible to vary source filtration, by quickly moving spectral filters in and out of the beam path. This will have the effect of presenting two different spectra to the detector given the selective nature across the energy spectrum of source filtration.

This approach can also be extended to multi-energy images by obtaining several sequential images at different kVp values or source filter, allowing for more spectral information to then algorithmically generate enhanced images.

Unfortunately, the temporal separation inherent in this technique causes motion artifacts to appear in the final images, which can pose a large challenge to a radiologist or observer interpreting it. These artifacts are noticeable distortions in the image caused by slight misalignments of the anatomies in the sequential images, and generally stem from patient or object motion that occurs during and in between image acquisitions.

Ideally, the source tube voltage could be changed instantaneously such that as soon as one exposure is finished, the next one can begin. However, current commercially-available sources require an interval between the successive exposures of at least 150 ms to 200 ms. This is due not only to a changing voltage but also because a change in tube current is also needed to achieve the ideal relative intensities of the images. While this interval is short enough for most patients to be able to refrain for large movements, cardiac, respiratory and small muscular motions are bound to occur throughout it. Motion artifacts will appear due to these movements, which can be a particular hindrance in cardiac and pulmonary imaging due to the large presence of the heart. Furthermore, this issue will compound as more image acquisitions are added in multi-energy imaging, since the total acquisition time will increase, allowing for more patient motion.

An alternative method for obtaining multi-energy images exists, which is commonly referred to as single-shot imaging. This method takes the opposite approach to multi-shot imaging and achieves spectral separation in the detector and not at the source. This is accomplished by stacking two sensor layers vertically to form a double-layer detector in what is known as a sandwich configuration. One layer, such as the top layer, absorbs mainly LE x-rays while the second layer, or the bottom layer, absorbs the HE x-rays. Therefore, only a single exposure is necessary with this technique, which is done at a higher kVp to allow for a large spectrum that covers both LE and HE x-rays. This method has since been expanded to multi-layer detectors that can obtain multiple images of increasing effective energy at subsequent stacked layers.

A practical issue that arises with the single-shot approach is that to obtain the ideal effective energy separation between the layers, the sensitive material—be it a scintillator or a direct conversion material—mass loading (or, equivalently, their thicknesses) must be tuned for specific tissue types and patient anatomy. Since at a commercial level it is only feasible to build a few specific configurations, this leaves a compromised solution that can best fit all target applications and patient types as the only practical one.

Therefore, there is provided a novel method and apparatus to mitigate or overcome at least one disadvantage of the imaging methods and apparatus described above.

SUMMARY OF THE DISCLOSURE

In one aspect of the disclosure, there is provided a method of determining at least one virtual output for a multi-energy x-ray imaging apparatus including receiving multiple outputs from the multi-energy imaging apparatus generated by different x-ray spectra; determining a general algorithm based on an x-ray imaging apparatus application, physical properties of the x-ray imaging apparatus or an x-ray source exposure settings; substituting the multiple outputs as inputs into the general algorithm to determine parameters and generate a virtual output algorithm for the multi-energy x-ray imaging apparatus and the determined application; and utilizing the virtual output algorithm to generate the at least one virtual output.

In another aspect, the multiple outputs received from the multi-energy x-ray imaging apparatus are obtained from some or all of the layers of the multi-energy x-ray imaging apparatus; and the multi-energy x-ray imaging apparatus is a single-shot multi-layer x-ray imaging apparatus. In a further aspect, the multiple outputs received from the multi-energy x-ray imaging apparatus are obtained from two or more x-ray exposures taken at different x-ray source exposure settings; and the multi-energy x-ray imaging apparatus is a multi-shot x-ray imaging apparatus. In another aspect, the x-ray source exposure settings include source voltage, source current or source filtration. In yet another aspect, determining the general algorithm includes determining the x-ray application that the multi-energy x-ray imaging apparatus is being used for; and selecting the general algorithm based on the determined application.

In another aspect, selecting the general algorithm includes selecting $S_i = c \cdot e^{-b \cdot l_i^a}$ for a multi-layer x-ray imaging apparatus (where a, b and c are parameter, $S_i$ is the signal at each layer and $l_i$ is the defined layer number) as the general algorithm. In another aspect, selecting the general algorithm includes selecting $$S_i = \int_{t_i^b}^{t_i^b + t_i} c \cdot e^{-b \cdot t^a} dt$$

for a multi-layer x-ray imaging apparatus (where b and c are parameter, $t_i^b$ is a thickness of a scintillator pre-filtering of each layer, and $t_i$ is a layer's scintillator thickness) as the general algorithm. In another aspect, determining the general algorithm includes selecting a minimization algorithm as the general algorithm.

In yet another aspect, utilizing the virtual output algorithm includes obtaining virtual outputs with a smaller of a noise component than the outputs obtained from the multi-energy x-ray imaging apparatus. In an aspect, utilizing the virtual output algorithm includes obtaining virtual outputs with a smaller object scattered radiation component than the outputs obtained from the multi-energy x-ray imaging apparatus. In an aspect, some or all of the at least one virtual output generated by the virtual output algorithm are used for the correction of faulty array pixels, lines or regions in one or more sensor layers of the multi-layer x-ray imaging apparatus. In yet another aspect, some or all of the at least one virtual output generated by the virtual output algorithm are used for obtaining bone mineral density or bone mineral area density measurements.

In another aspect of the disclosure, there is provided an x-ray imaging system for determining at least one virtual output for the x-ray imaging system including an x-ray source; a multi-energy x-ray imaging apparatus including at least one sensor layer; a processor for receiving multiple inputs from the x-ray imaging apparatus and for determining at least one virtual output for the x-ray imaging apparatus, the processor further including a computer readable medium having instructions stored therein that, if executed, cause the processor to: determine a general algorithm based on an x-ray imaging apparatus application, physical properties of the x-ray imaging apparatus and/or exposure settings of the x-ray source; substitute the multiple outputs of the multi-energy x-ray imaging apparatus as inputs into the general algorithm to determine parameters for a virtual output algorithm for the x-ray imaging apparatus and the determined application; and utilize the virtual output algorithm to generate the at least one virtual output.

In another aspect, the multi-energy x-ray imaging apparatus includes a set of sensor layers. In yet another aspect, the multi-energy x-ray imaging apparatus includes at least two sensor layers. In yet a further aspect, the multi-energy x-ray imaging apparatus further includes at least one mid-filter layer between at least two of the at least two sensor layers. In yet another aspect, the mid-filter layer includes a metallic material filter, a photoconductor layer or a scintillator layer. In yet another aspect, the multi-energy x-ray imaging apparatus further includes at least one anti-grid layer between at least two of the at least two sensor layers.

In an aspect, each of the at least one sensor layer includes a photoconductor layer or a scintillator layer. In another aspect, photoconductor or scintillator layers of adjacent sensor layers are adjacent each other. In a further aspect, at least one of the sensor layers includes a scintillator-infused glass substrate layer. In yet another aspect, at least one of the sensor layers includes a flexible substrate layer and an x-ray absorber.

DESCRIPTION OF THE DRAWINGS

Embodiments of the present disclosure will now be described, by way of example only, with reference to the attached Figures.

FIG. 5 is a schematic diagram of an indirect n-layer x-ray imaging apparatus and a direct n-layer x-ray imaging apparatus;

FIGS. 6a and 6b are schematic diagrams of different embodiments of an indirect 2-layer x-ray imaging apparatus and a direct 2-layer x-ray imaging apparatus;

FIG. 10a is a schematic diagram on an indirect n-layer x-ray imaging apparatus with mid-filters between the layers and a direct n-layer x-ray imaging apparatus with mid-filters between the layers;

FIGS. 10b and 10c are schematic diagrams of different embodiments of an indirect 3-layer x-ray imaging apparatus with mid-filter between some of the layers and a direct 3-layer x-ray imaging apparatus with mid-filter between some of the layers;

FIG. 11a is a schematic diagram on an indirect n-layer x-ray imaging apparatus with anti-scatter grids between the layers and a direct n-layer x-ray imaging apparatus with anti-scatter grids between the layers; and FIGS. 11b and 11c are schematic diagrams of different embodiments of an indirect 3-layer x-ray imaging apparatus with anti-scatter grid between some of the layers and a direct 3-layer x-ray imaging apparatus with anti-scatter grid between some of the layers;

DETAILED DESCRIPTION OF THE EMBODIMENTS

The disclosure is directed at a method and apparatus for determining virtual outputs for a multi-energy x-ray imaging apparatus. In one embodiment, the method receives actual outputs from the layers of a multi-layer x-ray imaging apparatus and then processes the outputs to determine outputs for other non-existent layers within the multi-layer x-ray imaging apparatus as if they were actual physical layers within the x-ray imaging apparatus. In another embodiment, the method receives actual outputs from different spectral/energy exposures obtained from a multi-shot imaging apparatus and then processes the outputs to determine the outputs for other non-obtained spectral/energy exposures.

Figure 8:
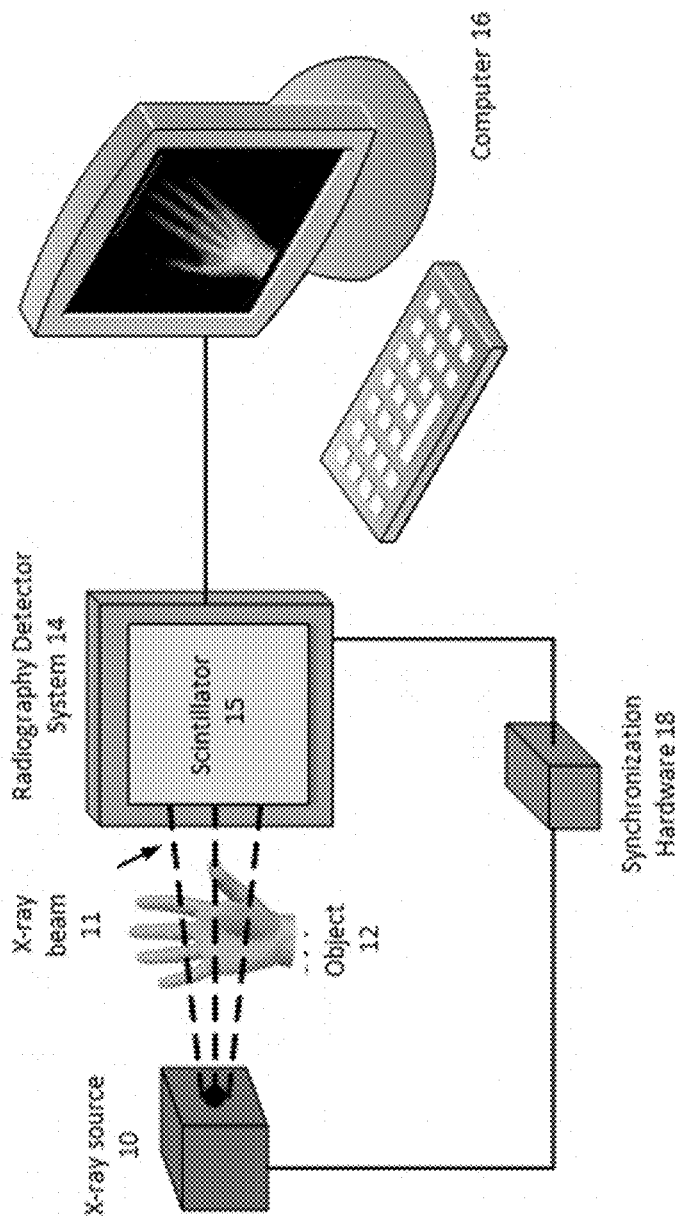
FIG. 8 illustrates a general diagram of a radiographic imaging environment.

FIG. 8 illustrates a general diagram of a radiographic imaging environment. As shown, an x-ray source 10 generates an x-ray beam, or x-rays, 11 that is transmitted towards an object 12, e.g. a patient's hand, for imaging by a radiography detector system (RDS) 14. The results of the x-ray exposure may be viewed on a computer or processor 16. In the current embodiment, which may be seen as an indirect imaging system, the radiography detector system 14 includes a scintillator 15. In a direct imaging system, the x-rays 11 generate electronic charge within the radiography detector system 14 and there is no need for the scintillator 15.

For some radiography detector systems 14, synchronization hardware 18 is necessary to obtain the correct timing between the x-ray source 10 and the radiography detector system 14 that is sampling the impinging x-ray beam 11. In the present disclosure, the radiography detector system 14 includes a large area, flat panel detector based on active matrix technologies to achieve the imaging of object 12.

In general, the object 12 to be imaged is positioned between the radiation source 10 and the radiography detector system 14. X-rays 11, which pass through the object 12, interact with the radiography detector system 14. In indirect imaging, the x-rays 11 generate light photons as they pass through a phosphor screen or scintillator 15, such as structured Cesium Iodide (CO, Gadolinium oxysulfide (GOS) or Calcium Tungsten Oxide ($CaWO_4$). These indirectly generated light photons then further generate electronic charge within the radiography detector system 14.

Figure 9:
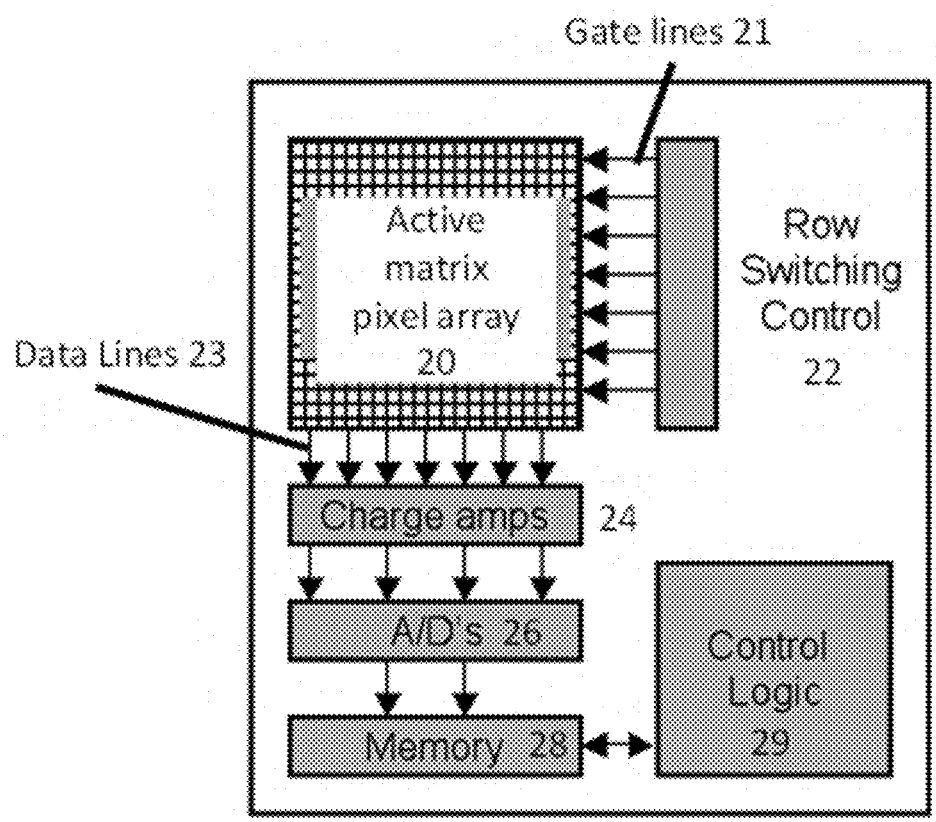
FIG. 9 illustrates a two-dimensional active matrix imaging array structure.

FIG. 9 is a schematic diagram of the radiography detector system 14. The RDS 14 includes an active matrix pixel array 20 having a two-dimensional matrix of pixel elements where electronic charges generated directly or indirectly by incident x-rays are sensed and stored. In order to access the stored charge at each pixel, gate lines 21 are driven typically sequentially by a row switching control 22 causing all pixels in one row to output their stored charge onto data lines 23 that are coupled to charge amplifiers 24 at the end of each active matrix pixel array 20 column. The charge amplifiers 24 send the pixel charge data to analog-to-digital converters (A/D's) 26, where the analog signal is converted to a digital representation. The digital representation is then stored in memory 28 awaiting transmission to the computer 16 at a time determined by the control logic 29. The charge amplifiers may also perform a multiplexing function in addition to their amplifying function.

Figure 1:
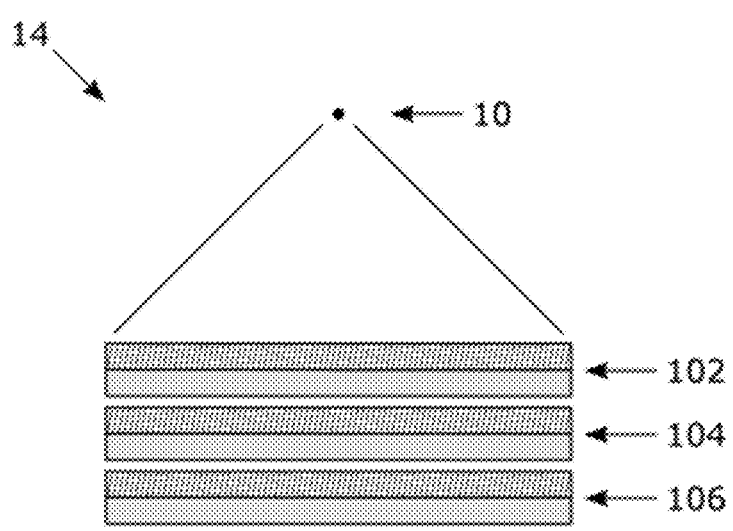
FIG. 1 is a schematic diagram of a triple-layer x-ray imaging apparatus.
Figure 2A:
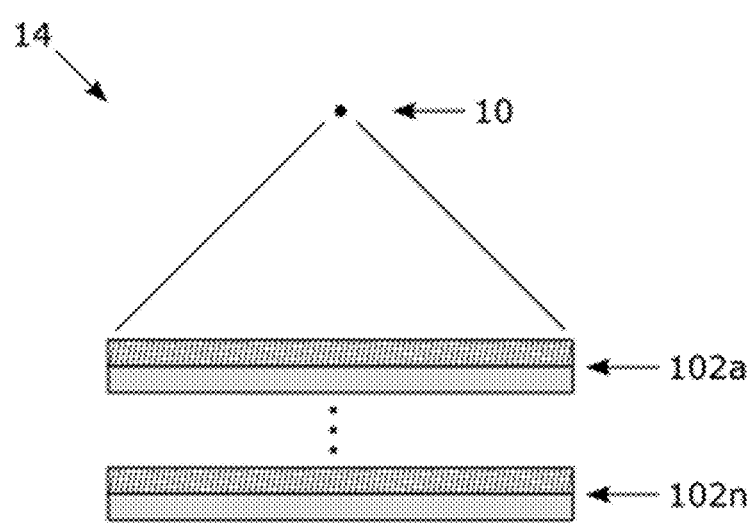
FIG. 2*a* is a schematic diagram of a multi-layer x-ray imaging apparatus, which represents an x-ray imaging apparatus with two or more layers.

Turning to FIG. 1, a schematic diagram of a multi-layer x-ray imaging detector element, or apparatus, is shown. In the current embodiment, the detector element 14 includes three different sensor layers, seen as a top layer 102, an intermediate, or middle, layer 104 and a bottom layer 106. As will be understood, in a preferred embodiment, each of the top layer 102, the intermediate layer 104 and the bottom layer 106 are the same as each other. Each of the sensor layers can be seen as an individual layer of a multi-layer x-ray detector element or imaging detector. In one embodiment each layer may be an amorphous silicon (a-Si) flat-panel sensor layer coupled to a scintillator layer. Alternatively, any type of indirect or direct conversion x-ray detection layer may be used for the individual layers. In other embodiments, shown in FIG. 2a, the detector can include any number of stacked sensor layers (all labelled as 102a to 102n where n can be any number), each with its indirect or direct conversion material. During operation, each layer will produce an output that can be used by a method of the disclosure to obtain further virtual outputs.

Figure 2B:
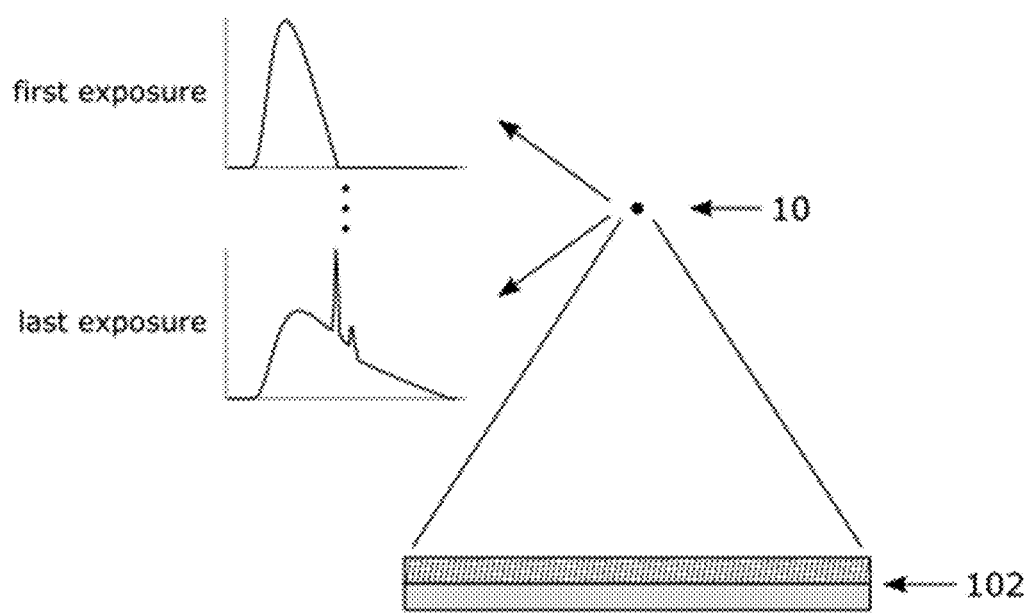
FIG. 2*b* is a schematic diagram of a multi-shot x-ray imaging apparatus, which represents an x-ray imaging system where two or more exposures are obtained at different source voltages, currents and/or filtrations.

Alternatively, the x-ray imaging apparatus may be part of a multi-shot imaging system. In this case, the detector includes only one sensor layer, but multiple images are obtained by changing the X-ray source properties (such as, but not limited to, kVp and/or filtration) and re-exposing. Each of these images can be considered as an output from the detector which can then be used by the presented method to obtain further virtual outputs representing other source properties. A schematic diagram of an x-ray imaging detector for use in a multi-shot imaging system is shown in FIG. 2b.

Figure 3A:
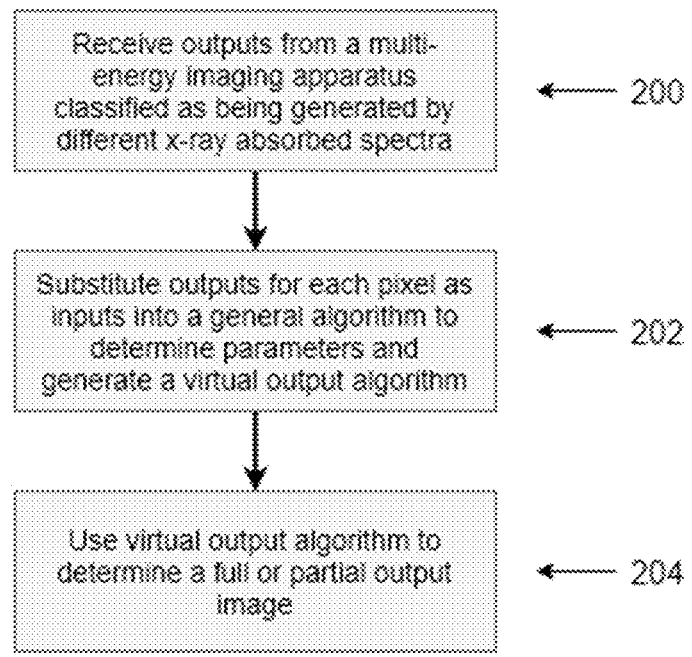
FIG. 3a is a flowchart outlining a method of determining virtual image outputs for a multi-energy x-ray imaging apparatus.
Figure 3B:
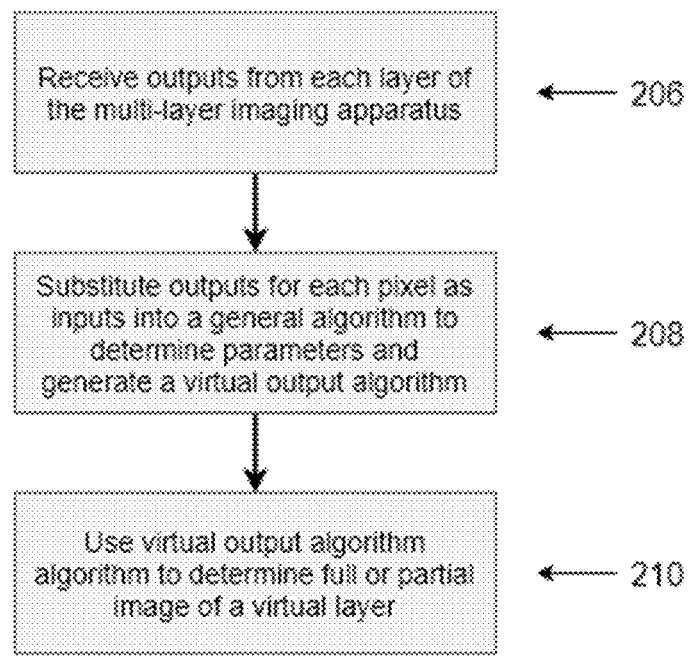
FIG. 3b is a flowchart outlining a method of determining virtual layer outputs for a multi-layer x-ray imaging apparatus.

Turning to FIG. 3a, a flowchart is shown outlining the basic steps of a method of the disclosure and how it may be used with a multi-energy x-ray imaging apparatus or system to generate at least one virtual output. FIG. 3b is a flowchart outlining a method of determining outputs for at least one virtual layer. In this embodiment, the method may be used for x-ray detector elements or x-ray imaging apparatus having two or more sensor layers. In one embodiment, the method and apparatus of the disclosure overcomes the challenges of using an x-ray detector imaging apparatus having different x-ray absorber thicknesses. In one embodiment, the method may allow for simpler multi-layer detector designs with more versatile and improved multi-energy imaging capabilities.

Initially, the x-ray imaging apparatus is exposed to an x-ray source such that outputs from each of the layers are read by readout electronics, such as, but not limited to, a readout array, to a processor. In other words, the system receives inputs (seen as the layer outputs) from the multi-energy imaging apparatus that may be classified as being generated by different x-ray absorbed spectra (200).

Based on the application that the x-ray imaging apparatus is being used for, the processor can then enter, or substitute the inputs into a, preferably, predetermined or preselected, general algorithm or equation to determine a virtual output algorithm for the x-ray apparatus (204). This means calculating or determining the parameters for the general algorithm. The general algorithm may be selected based on any of: the application of the x-ray imaging device; the physical characteristics of the x-ray imaging device or system; and/or the specific x-ray source settings used in one or more exposures. Once these parameters are calculated, they may be entered into or used in the general algorithm to determine or generate a virtual output algorithm. The virtual output algorithm can then be used to calculate the expected (or virtual) outputs, such as an image, for other virtual layers of the x-ray imaging apparatus (204).

To assist in the understanding of the method, an example embodiment of the method is provided. An overview of the amount of signal remaining in an x-ray beam after it has passed through an object as it is absorbed in a single, infinitely thick scintillator is provided. The amount of signal remaining at any point in the beam path is defined as $$S = \int_0^\infty \Phi(E) \cdot \overline{Q}(E) dE$$

where $\Phi(E)$ is the spectrum of the remaining beam, and $\overline{Q}(E)$ is the mean scintillator gain function, which is typically of the form $\overline{Q}(E) \propto E$ for common inorganic scintillators.

Figure 4A:
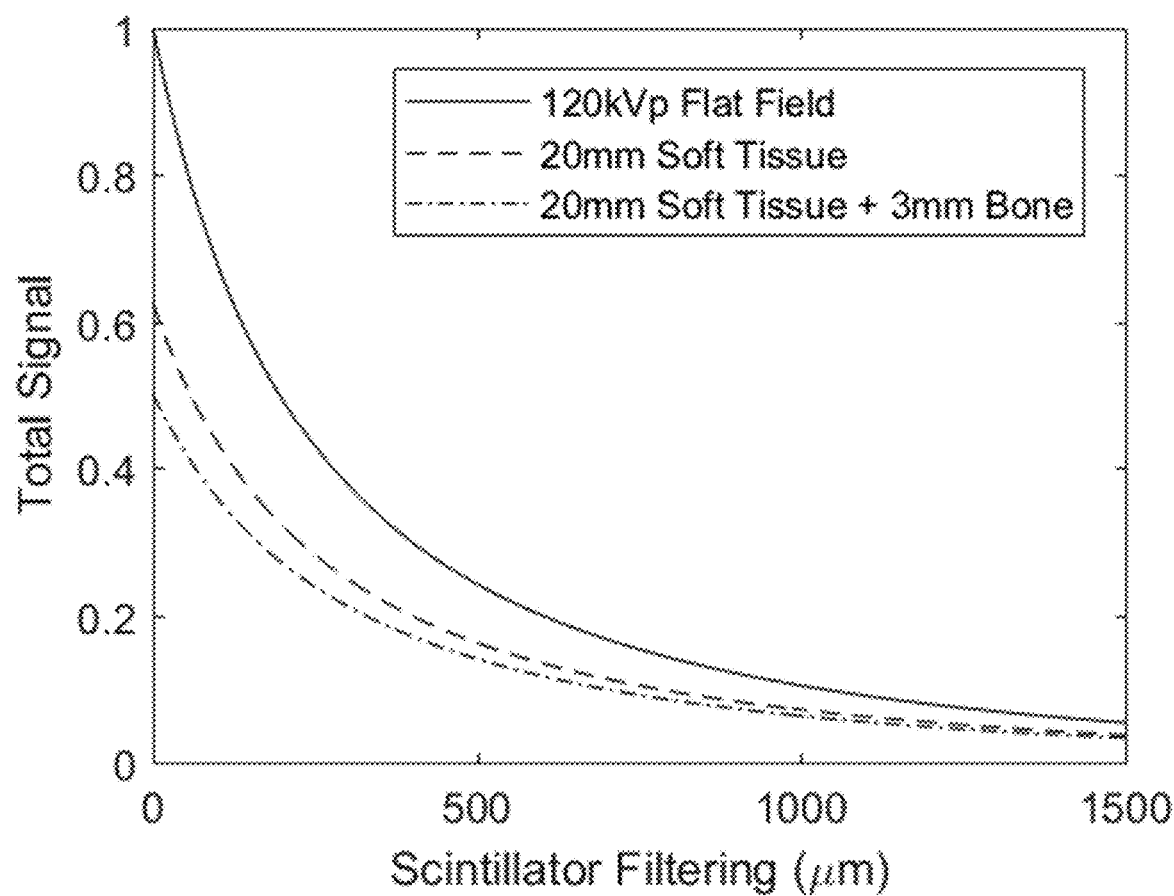
FIG. 4a is a graph outlining an example Total Signal vs Scintillator Filtering.
Figure 4B:
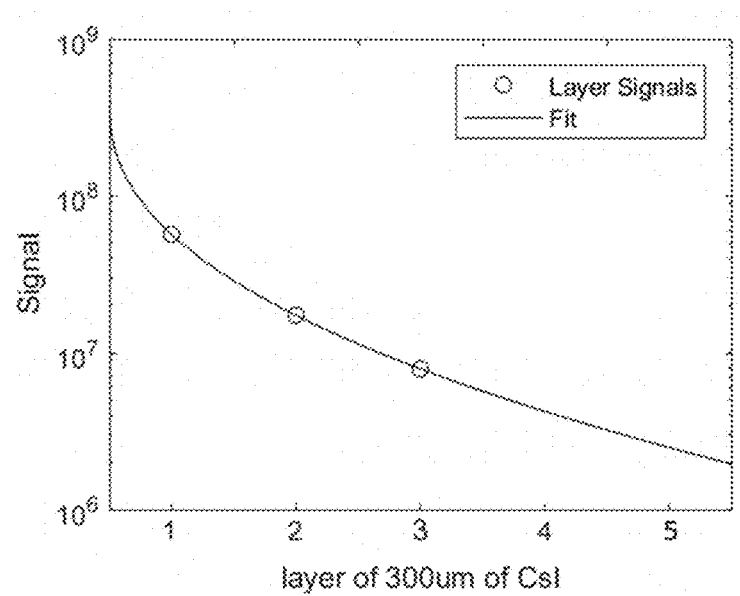
FIG. 4b is a graph of an example equation fit for sample outputs of a three-layer detector.

As can be seen in FIG. 4a, this signal decays exponentially as it travels through this absorber. By considering an embodiment of a multi-layer detector with layers of the same scintillator material and thickness, the signal obtained at each layer ($S_i$) can be used to generate an equation that will describe its trend. It is expected that the signal at each layer to be decreasing exponentially, with a rate of exponential decrease that will change as the amount of signal in the beam decreases. This is because the signal at each layer will be the difference in values of two points on the curves shown in FIG. 4a. Therefore, the equation chosen in this example is $$S_i = c \cdot e^{-b \cdot l_i^a}.$$

where the value $l_i$ in this equation is called the layer number. Mathematically, the layer number corresponds to the total scintillator thickness of each layer. However, given that the parameters a, b and c are being fit, $l_i$ is normalized to the layer thickness for simplicity whereby $l_i=1, 2, 3$. As will be understood, this is merely for simplicity and is not required for this method. In practice, the values for $l_i$ may be modified to account for x-ray losses in detector elements other than the scintillators and other non-idealities. By substituting the received outputs into the general equation or algorithm shown above, the parameters for the virtual output equation can be determined in order to provide a virtual output equation that may be used for generating any virtual layer of the detector. FIG. 4b shows an example of how once the parameters for this fitting equations are found, it can be used to approximate values for virtual layers.

Once fit, the found parameters for each pixel can be used to generate the image of a virtual detector layer of any chosen thickness and with any chosen amount of pre-filtering. As such, a virtual output algorithm for the x-ray imaging apparatus and the application that the x-ray imaging apparatus is being used for can be found and then used to calculate values for virtual layers. For example, an infinitely thick bottom layer can be computed with $\Sigma_{i=3}^\infty S_i$, or a top layer of half the thickness can be computed using $$\sum_{i=\frac{1}{2}}^\infty S_i - \sum_{i=1}^\infty S_i.$$

Note that even though the virtual output equation directly gives the signal for a layer of the same thickness as those that built up the detector, by intelligently using this equation, it is possible to indirectly obtain values for a layer of any desired thickness.

Therefore, an advantage of the current disclosure is that it can facilitate the computation of a virtual multi-layer detector element with any arbitrary number of layers of arbitrary thicknesses, and even of physically-impossible detector configurations such as superimposed layers or infinitely thick layers. This can be a benefit or advantage for both dual-energy techniques—where the virtual thicknesses can be tailored to generate the best possible tissue-subtracted images—and to digital radiography techniques—where the quality of the image may be improved by generating an impractically thick single virtual layer or by intelligently reducing noise by means of a more complex fitting method.

Turning to FIG. 3b, a flowchart outlining a method of determining virtual layer outputs for a multi-layer x-ray imaging apparatus is shown. Initially, inputs (such as the outputs from athe multi-layer x-ray detector being exposed to an x-ray source) are received from each layer of the multi-layer imaging apparatus (206). These inputs (or outputs) are then substituted for each pixel as inputs into a general algorithm to determine parameters for and to generate a virtual output algorithm (208). The virtual output algorithm can then be used to generate a full or partial image of would be generated by a virtual layer (210).

Figure 3C:
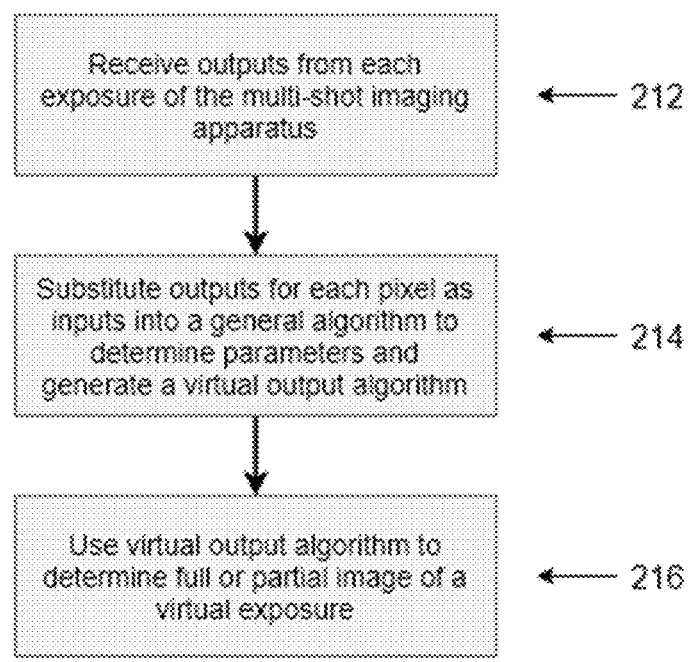
FIG. 3c is a flowchart outlining a method of determining virtual energy outputs for a multi-shot x-ray imaging apparatus.

Turning to FIG. 3c, flowchart outlining a method of determining virtual energy outputs for a multi-shot x-ray imaging apparatus is shown. Initially, the outputs from each exposure of a multi-shot imaging apparatus are received (212). These outputs are then substitute for each pixel as inputs into a general algorithm to determine parameters for and to generate a virtual output algorithm (214). The virtual output algorithm can then be used to determine a full or partial image for a virtual exposure (216)

While some mathematical implementations or equations to describe signal-change are disclosed with respect to FIG. 3a, 3b or 3c, any number of equations or algorithms may be used as the general algorithm. These general equations or algorithms may require different number(s) of fitting parameters and may be of varying fit quality. Some will fit the input signals exactly, while other may approximate a new signal curve by using the signals as references. However, they are all similar in that they take the outputs of the different layers or energy exposures as inputs or signals as well as physical information of the detector and its operation such as layer scintillator thickness and materials, or different source voltages or filtrations used.

Moreover, it should be noted that although the disclosed embodiment discusses use of a multi-layer detector with all equal absorbers to obtain the necessary fit, other configurations of varying sensor type and thickness are contemplated and may improve the fit accuracy and allow for more sophisticated fitting algorithms. The method of the flowchart in FIG. 3b can also be useful even if only two layers are utilized. Similarly, the method in the flowchart in FIG. 3c may be used for a multi-shot switching detector system as shown in FIG. 2b, where any number of exposures at different source voltages, currents and/or filtrations may be used as inputs to the algorithms that can then generate virtual exposure images.

In a multi-layer detector with fewer layers, and therefore fewer outputs to be used by the general algorithm, the algorithmic fitting accuracy may be low. However, this can be improved by, for example, using a known material as a mid-filter to spectrally separate the beam spectrum between detector layers, allowing for a wider spectral coverage of the signals to the algorithm. As long as the physical configuration of the detector apparatus is known, the general algorithm may be adapted in order to accommodate any configuration and generate an appropriate virtual output algorithm that allows for the calculation of a virtual layer signal. Similarly, as long as the exposure setting (such as voltages, currents and filtrations) are known in a multi-shot imaging system, a general algorithm can be selected to accommodate the chosen parameters and generate a virtual output algorithm that allow for the computation of virtual exposure signals.

The embodiment presented above is an example that serves to illustrate this technique. As mentioned, the implementation details of the method of the disclosure can be modified to allow for better results in a specific application or given a specific detector system. The simplest modification to the example provided would be to modify the general equation or algorithm to another exponentially-decreasing equation such as $$S_i = c \cdot e^{-b \cdot l_i^a}.$$

Another example is using a multi-layer detector with scintillators of same or different thicknesses to fit the amount of signal in the beam as opposed to the absorbed signals, thereby approximating the curves in FIG. 4a with a fit equation, and assuming the signal at each layer will be a definite integral of the curve which, may for example leave the general algorithm as:

$$S_i = \int_{t_i^b}^{t_i^b + t_i} c \cdot e^{-b \cdot t^a} dt$$

where $t_i^b$ is the thickness of scintillator pre-filtering of each layer, and $t_i$ is the layer's scintillator thickness.

Furthermore, the method of the disclosure can be modified for use with a multi-layer detector having scintillators of both different materials and thicknesses. In this case, the input x-ray spectrum at each pixel may be fit to a parametrized function. This is possible because the signal at each layer is known to be proportional to the product of the remaining spectrum at each layer and the absorption efficiency of the layer.

In another embodiment, a multi-layer detector of two or more layers may be used and the signals obtained used to find the best fit parameters for $S_i = c \cdot e^{-b \cdot l_i}$.

In a further implementation, a dual-layer detector may be used with a mid-filter made of the same scintillator material, and fitting the signals to the equation $S_i = c \cdot e^{-b \cdot l_i}$ but using $l_i = 1, 5$ for the top and bottom signals respectively. This effectively still leaves $S_i$ normalized to double layer thickness. Again, note that $l_i$ values may be modified in practice to account for other detector elements. This implementation can be extended to the previously-mentioned implementation of assuming the signal at each layer is a definite integral of a curve with fit parameters, but accounting the middle scintillator material in the integral limit selection by adding its thickness to the limits of the integral for those layers after this mid-filter in the beam path. It can further be extended by utilization of different parametrized equations for $S_i$.

In another embodiment, a quadruple-layer detector may be used and fitting the signals to any of the previously-mentioned general equations, or a new equation with four parameters, such as $S_i = c \cdot e^{-b \cdot l_i^d} \cdot l_i^a$. In yet another embodiment, more complex general algorithms are also possible, such as minimization algorithm, as in the form of Monte Carlo minimization algorithms.

Through these examples, it is clear that different types of mathematical methods can be used in conjunction to any multi-layer x-ray detector to generate virtual layer signals. It will also be understood that the method of the disclosure can be expanded to any multi-energy detector system, including, but not limited to, multi-shot imaging systems, where separate image exposures are taken at different source voltages, currents and/or filtrations. This method can fit for a trend between different input spectra, and hence allow for extrapolation to other input source voltages and for a better understanding of the materials being imaged. As should be evident, the approach taken by the method of the disclosure is also equally valid in further applications, such as multi-spectral 3D computed tomography imaging, or real-time imaging.

Furthermore, the method of the disclosure can be uses to algorithmically transfer information between layers or exposures while maintaining local contrast. This allows for correction of other issues typically encountered in x-ray imaging, including the correction of faulty array pixels, lines or regions, or reducing electronic or quantum noise. Array fault correction can allow for the relaxation of low or minimum defect density requirements on individual sensor layers. A similar improvement can be obtained for noise reduction, where data from multiple layers or multiple exposures can reduce the uncertainty in the measurement of the true signal.

One way in which the method of the disclosure may be used to correct for faulty array pixels, lines or regions in individual sensor layers in a multi-layer x-ray detector apparatus is by: first, identifying the individual faulty pixels, or all pixels belonging to faulty lines or regions, in one sensor layer; taking the outputs corresponding to those pixels or regions from all other sensor layers in the multi-layer detector apparatus, where an output from one layer corresponds to that in another layer if their values correspond to a similar section of the object being imaged; fitting these outputs to a general algorithm to generate a virtual output algorithm; using the virtual algorithm to obtain the virtual outputs for all faulty pixels or regions to match the physical characteristics of the original sensor layer; and replacing the values of the faulty pixels in the original sensor layer with the virtual outputs. It is clear that this method may be reproduced for each individual sensor layer to remove all faulty pixel values from some or all layers of a multi-layer detector apparatus.

Noise reduction in sensor output data may also be achieved by utilizing the method of the disclosure. This may be done by selecting a general algorithm that requires fewer fitting parameters than the number of layers in a multi-layer imaging apparatus or exposures in a multi-shot imaging system, or by selecting one that does not weigh all output data in an equal manner. Once the virtual output algorithm for this general algorithm is found, a virtual output layer or exposure may be generated with the same or similar physical characteristics to one of the apparatus outputs. By the nature of the general algorithm selected, this virtual output may have similar local contrast as the original apparatus output but with a smaller of a noise component. It may also be possible to replace only certain regions or spatial frequency components of the original output to achieve better results.

One additional application of the method of the disclosure is for the measurement of bone mineral density through dual-energy x-ray absorptiometry. Either the found parameters for a virtual output algorithm, or the generated virtual layer or exposure images may be used in conjunction with any additional information about the x-ray imaging apparatus, about the exposure settings used, or about the x-ray system configuration to compute density or area density in some or all of the boney regions imaged.

A further application of this method of the disclosure is object scatter correction. X-ray radiation is typically scattered off the object being imaged, contributing to an overall loss in image quality. The difference in spectral characteristics in typical object scattered radiation can be exploited by the method of the disclosure to isolate and therefore remove it from the final output image, thereby improving image quality.

Figure 7A:
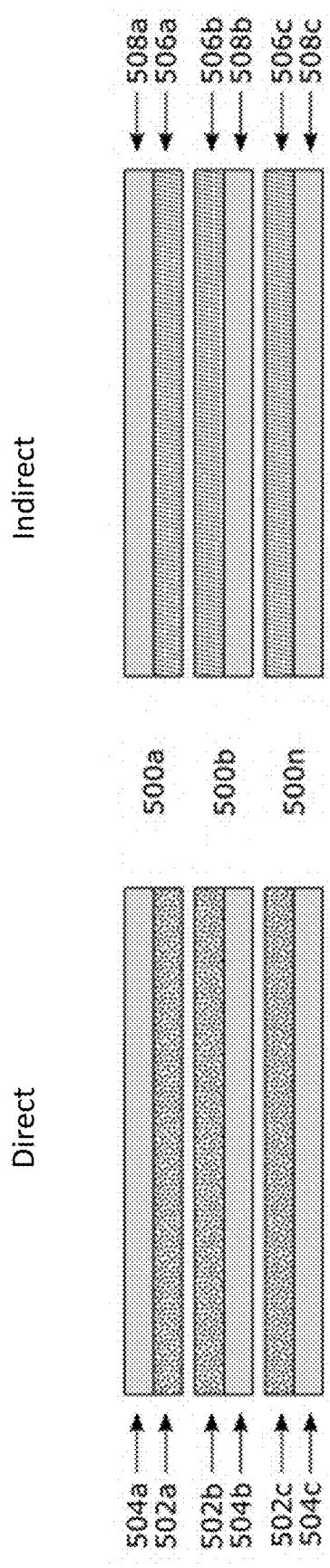
FIGS. 7a and 7b are schematic diagrams of different embodiments of an indirect 3-layer x-ray imaging apparatus and a direct 3-layer x-ray imaging apparatus.
Figure 7B:
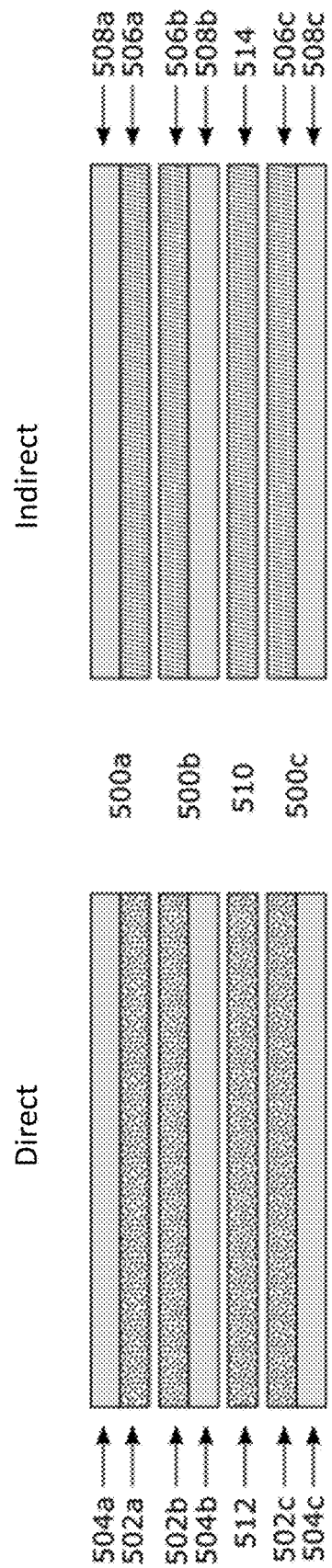

Different multi-layer detectors that may be used with the method of the disclosure are schematically shown in FIG. 5 (n-layers), FIGS. 6a and 6b (two-layer approach) and FIGS. 7a and 7b (triple-layer approach) for both indirect scintillator-based x-ray detectors and direct photoconductor-based x-ray approaches. Given the nature of the materials used, it is expected that some amount of scattered or fluorescent radiation (hereon grouped under the first term) from one layer to another will be present when exposing the detector, thereby changing the signal outputs from each layer, which may affect the method presented here for determining virtual outputs.

As shown in FIG. 5, the detector 14 includes "n" sensor layers 500a, 500b, 500n. As will be understood, "n" represents any number. For a direct multi-layer x-ray detector, each sensor layer 500 includes a photoconductor layer 502 and a substrate layer 504. For an indirect multi-layer x-ray detector, each sensor layer 500 includes a scintillator layer 506 and a substrate layer 508.

As shown in FIG. 6a, the detector includes a first sensor layer 500a, a mid-filter layer 510 and a second sensor layer 500b. For a direct multi-layer x-ray detector, each sensor layer 500 includes a photoconductor layer 502 and a substrate layer 504. In the current embodiment, the mid-filter layer 510 may be another photoconductor layer 512. For an indirect multi-layer x-ray detector, each sensor layer 500 includes a scintillator layer 506 and a substrate layer 508 where the mid-filter layer 510 may be another scintillator layer 514.

The embodiment shown in FIG. 6b is similar to the embodiment of FIG. 6a with the positions of the photoconductor layer 502 and the substrate layer 504 (direct) and the positions of the scintillator layer 506 and the substrate layer 508 (indirect) switched within the sensor layers 500.

As shown in FIG. 7a, the detector includes a first sensor layer 500a, a second sensor layer 500b and a third sensor layer 500c. For the direct multi-layer x-ray detector, each sensor layer 500 includes a photoconductor layer 502 and a substrate layer 504. For the indirect multi-layer x-ray detector, each sensor layer 500 includes a scintillator layer 506 and a substrate layer 508.

The embodiment shown in FIG. 7b is similar to the embodiment of FIG. 7a with an added mid-filter layer between the second 500b and third 500c sensor layers. As will be understood, the mid-filter layer may also be placed between the first 500a and second 500b sensor layers. Alternatively, mid-filter layers 510 may be placed between both the first and second sensor layers and the second and third sensor layers.

To overcome the challenge of reducing or minimizing radiation scattered by the x-ray absorbing layers, various strategies may be employed. One strategy may be to select a material with a low k-edge (such as amorphous selenium photoconductor) where k-fluorescent x-rays have an energy of <12 keV and thus do not travel far, or alternatively, CsI scintillator with 33 keV fluorescent x-rays. Also, mid-filters made of the same material as the scintillator of choice may be employed to reduce the effects of scattered radiation. Furthermore, the orientation of the sensor layers can be changed as schematically shown in FIGS. 6a, 7a and 7b, where the sensor layer 500a is oriented such that the distance between photoconductor layers 502 (direct) or scintillator layers 506 (indirect) is minimized, reducing scattered distance associated with the x-ray k-fluorescence.

Further techniques can be used to reduce cross-scatter between the layers. This includes the addition of anti-scatter grids in between the sensor layers in any of the configurations mentioned previously, as shown in FIGS. 11a, 11b and 11c, which will disproportionally absorb scatter radiation and hence reduce the proportion of the layer's signal values that correspond to scatter (known as the scatter-to-primary ratio).

FIG. 11a is a schematic diagram of a multi-layer detector 500 including a plurality of sensor layers 500a, 500b, . . . , 500n, where "n" can be any number. Located between the sensor layers 500 are the anti-scatter grid layers 516. As with previous embodiments, each direct sensor layer includes a photoconductor layer 502 and a substrate layer 504 and each indirect sensor layer includes a scintillator layer 506 and a substrate layer 508.

FIG. 11b is a schematic diagram of a multi-layer detector 500 including three (3) sensor layers 500a, 500b and 500c and a single anti-scatter grid layer 516 between the first and second sensor layers. FIG. 11c is a schematic diagram of a multi-layer detector 500 including three (3) sensor layers 500a, 500b and 500c and a single anti-scatter grid layer 516 between the second and third sensor layers.

Similarly, mid-filters may be added in between the sensor layers as shown in FIGS. 10a, 10b and 10c which will disproportionally absorb scattered photons since these are mainly of energies in the lower end of the diagnostic x-ray spectrum. The specific material type of the mid-filters may be selected to tune scatter energy absorption. In one embodiment, the material choice for one or more mid-filters is metallic, such as copper, aluminum, or silver.

FIG. 10a is a schematic diagram of a multi-layer detector 500 including a plurality of sensor layers 500a, 500b, ..., 500n, where "n" can be any number. Located between the sensor layers 500 are the mid-filter layers 518. As with previous embodiments, each direct sensor layer includes a photoconductor layer 502 and a substrate layer 504 and each indirect sensor layer includes a scintillator layer 506 and a substrate layer 508.

FIG. 10b is a schematic diagram of a multi-layer detector 500 including three (3) sensor layers 500a, 500b and 500c and a single mid-filter layer 518 between the first and second sensor layers. FIG. 11c is a schematic diagram of a multi-layer detector 500 including three (3) sensor layers 500a, 500b and 500c and a single mid-filter layer 518 between the second and third sensor layers.

Another technique is to reduce or minimize the distance between x-ray absorber layers by utilizing as thin a substrate as possible, where it is possible to reduce their thicknesses significantly by using flexible substrates. Lastly, this distance may be removed completely by combining the substrate and absorber layers in the form of scintillator-infused substrates.

In the preceding description, for purposes of explanation, numerous details are set forth in order to provide a thorough understanding of the embodiments. However, it will be apparent to one skilled in the art that these specific details may not be required. In other instances, well-known structures may be shown in block diagram form in order not to obscure the understanding. For example, specific details are not provided as to whether elements of the embodiments described herein are implemented as a software routine, hardware circuit, firmware, or a combination thereof.

Embodiments of the disclosure or components thereof can be provided as or represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor or controller to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor, controller or other suitable processing device, and can interface with circuitry to perform the described tasks.

The above-described embodiments are intended to be examples only. Alterations, modifications and variations can be effected to the particular embodiments by those of skill in the art without departing from the scope, which is defined solely by the claims appended hereto.

What is claimed is:

1. A method of determining at least one virtual output for a multi-energy x-ray imaging apparatus:
   receiving multiple outputs from the multi-energy imaging apparatus generated by multiple dissimilar absorbed x-ray spectra;
   determining a general algorithm based on an x-ray imaging apparatus application, physical properties of the x-ray imaging apparatus or an x-ray source exposure settings;
   substituting the multiple outputs as inputs into the general algorithm to determine parameters and generate a virtual output algorithm for the multi-energy x-ray imaging apparatus and the determined application; and
   utilizing the virtual output algorithm and at least one input based on an X-ray spectrum property to generate the at least one virtual output.

2. The method of claim 1 wherein the multiple outputs received from the multi-energy x-ray imaging apparatus are obtained from some or all of the layers of the multi-energy x-ray imaging apparatus; and
   wherein the multi-energy x-ray imaging apparatus is a single-shot multi-layer x-ray imaging apparatus.

3. The method of claim 2 wherein some or all of the at least one virtual output generated by the virtual output algorithm are used for the correction of faulty array pixels, lines or regions in one or more sensor layers of the multi-layer x-ray imaging apparatus.

4. The method of claim 1 wherein the multiple outputs received from the multi-energy x-ray imaging apparatus are obtained from two or more x-ray exposures taken at different x-ray source exposure settings; and
   wherein the multi-energy x-ray imaging apparatus is a multi-shot x-ray imaging apparatus.

5. The method of claim 4 wherein the x-ray source exposure settings comprise source voltage, source current or source filtration.

6. The method of claim 1 wherein determining the general algorithm comprises:
   determining the x-ray application that the multi-energy x-ray imaging apparatus is being used for; and
   selecting the general algorithm based on the determined application.

7. The method of claim 6 wherein selecting the general algorithm comprises:
   selecting $S_i = c \cdot e^{-b \cdot l_i^a}$ for a multi-layer x-ray imaging apparatus (where a, b and c are parameter, $S_i$ is the signal at each layer and $l_i$ is the defined layer number) as the general algorithm.

8. The method of claim 6 wherein selecting the general algorithm comprises:
   selecting $S_i = c \cdot e^{-b \cdot l_i}$ for a multi-layer x-ray imaging apparatus (where b and c are parameter, $S_i$ is the signal at each layer and $l_i$ is the defined layer number) as the general algorithm.

9. The method of claim 6 wherein selecting the general algorithm comprises:
   selecting $$S_i = \int_{t_i^b}^{t_i^b + t_i} c \cdot e^{-b \cdot t^a} dt$$

dt for a multi-layer x-ray imaging apparatus (where b and c are parameter, $t_i^b$ is a thickness of a scintillator pre-filtering of each layer, and $t_i$ is a layer's scintillator thickness) as the general algorithm.

10. The method of claim 6 wherein determining the general algorithm comprises:
   selecting a minimization algorithm as the general algorithm.

11. The method of claim 1 wherein utilizing the virtual output algorithm comprises:
   obtaining virtual outputs with a smaller of a noise component than the outputs obtained from the multi-energy x-ray imaging apparatus.

12. The method of claim 1 wherein utilizing the virtual output algorithm comprises:
   obtaining virtual outputs with a smaller object scattered radiation component than the outputs obtained from the multi-energy x-ray imaging apparatus.

13. The method of claim 1 wherein some or all of the at least one virtual output generated by the virtual output algorithm are used for obtaining bone mineral density or bone mineral area density measurements.

14. An x-ray imaging system for determining at least one virtual output for the x-ray imaging system comprising:
   an x-ray source;
   a multi-energy x-ray imaging apparatus including at least one sensor layer;
   a processor for receiving multiple inputs from the x-ray imaging apparatus generated by multiple dissimilar absorbed x-ray spectra and for determining at least one virtual output for the x-ray imaging apparatus, the processor further including a computer readable medium having instructions stored therein that, if executed, cause the processor to:
   determine a general algorithm based on an x-ray imaging apparatus application, physical properties of the x-ray imaging apparatus and/or exposure settings of the x-ray source;
   substitute the multiple outputs of the multi-energy x-ray imaging apparatus as inputs into the general algorithm to determine parameters for a virtual output algorithm for the x-ray imaging apparatus and the determined application; and
   utilize the virtual output algorithm and at least one spectral input based on an X-ray spectrum property to generate the at least one virtual output.

15. The x-ray imaging system of claim 14 wherein the multi-energy x-ray imaging apparatus comprises:
   a set of sensor layers.

16. The x-ray imaging system of claim 15 wherein the multi-energy x-ray imaging apparatus comprises:
   at least two sensor layers.

17. The x-ray imaging system of claim 16 wherein the multi-energy x-ray imaging apparatus further comprises:
   at least one mid-filter layer between at least two of the at least two sensor layers.

18. The x-ray imaging system of claim 17 wherein the mid-filter layer comprises a metallic material filter, a photoconductor layer or a scintillator layer.

19. The x-ray imaging system of claim 16 wherein the multi-energy x-ray imaging apparatus further comprises:
   at least one anti-grid layer between at least two of the at least two sensor layers.

20. The x-ray imaging system of claim 16 where at least one of the sensor layers comprises a scintillator-infused glass substrate layer.

21. The x-ray imaging system of claim 16 where at least one of the sensor layers comprises a flexible substrate layer and an x-ray absorber.

22. The x-ray imaging system of claim 15 wherein each of the at least one sensor layer comprises:
   a photoconductor layer or a scintillator layer.

23. The x-ray imaging system of claim 22 wherein photoconductor or scintillator layers of adjacent sensor layers are adjacent each other.

* * * * *